US00PP30142P2

(12) United States Plant Patent
Kordes

(10) Patent No.: US PP30,142 P2
(45) Date of Patent: Jan. 29, 2019

(54) GRANDIFLORA ROSE PLANT NAMED 'KORROLEOTU'

(50) Latin Name: *Rosa hybrida*
Varietal Denomination: KORroleotu

(71) Applicant: W. KORDES' SÖHNE Rosenschulen GmbH & Co KG, Klein Offenseth-Sparrieshoop (DE)

(72) Inventor: Wilhelm-Alexander Kordes, Klein Offenseth-Sparrieshoop (DE)

(73) Assignee: W. KORDES' SÖHNE Rosenschulen GmbH & Co KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 15/732,095

(22) Filed: Sep. 18, 2017

(51) Int. Cl.
*A01H 5/02* (2018.01)

(52) U.S. Cl.
USPC ..... Plt./140
CPC ..... *A01H 5/02* (2013.01)

(58) Field of Classification Search
USPC ..... Plt./140, 139
CPC ..... A01H 5/0222
See application file for complete search history.

(56) References Cited

U.S. PATENT DOCUMENTS

PP22,828 P2 7/2012 Kordes

*Primary Examiner* — Kent L Bell
(74) *Attorney, Agent, or Firm* — Buchanan Ingersoll & Rooney PC

(57) ABSTRACT

A new and distinct variety of Grandiflora Rose Plant, herein referred to by its cultivar name, 'KORroleotu', is provided which forms in abundance on a substantially continuous basis attractive, red colored blossoms. The vegetation is vigorous and the growth habit is very bushy and upright. Attractive glossy, dark green foliage is formed. The resistance to disease is very good. The new variety is particularly well suited for providing distinctive ornamentation in the landscape.

2 Drawing Sheets

Botanical/commercial classification:
Latin name—*Rosa hybrida.*
Common name—Grandiflora Rose Plant.
Varietal denomination—'KORroleotu'.

SUMMARY OF THE INVENTION

The new variety of *Rosa hybrida* Grandiflora Rose Plant of the present invention was created during May 2007 at Offenseth-Sparrieshoop, Germany by artificial pollination wherein two parents were crossed which previously had been studied in the hope that they would contribute the desired characteristics. The female parent (i.e., seed parent) of the new variety was the 'MEIangele' variety (non-patented in the United States). The male parent (i.e., pollen parent) was the 'KORtutu' variety (U.S. Plant Pat. No. 22,828).

The parentage can be summarized as follows:

'MEIangele' x 'KORtutu'

The seeds resulting from the above pollination were sown and small plants were obtained which were physically and biologically different from each other. Selective study resulted in the identification of a single plant of the new variety.

It was found that the new Grandiflora Rose Plant of the present invention possesses the following combination of characteristics:

(a) abundantly and substantially continuously forms attractive, red colored blossoms,
(b) exhibits a very bushy and upright growth habit,
(c) forms vigorous vegetation, (d) forms attractive ornamental glossy, dark green foliage, and
(e) exhibits very good disease resistance.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors. More specifically, the 'MEIangele' variety (i.e., seed parent) displays smaller flowers, smaller foliage, and a more compact growth habit than that of the new variety. Additionally, the new variety exhibits a lighter red flower color, a more nostalgic flower shape, and a higher petal count than that of the 'KORtutu' variety (i.e., pollen parent).

The new variety has been found to undergo asexual propagation in Klein Offenseth-Sparrieshoop, Germany by a number of routes such as budding. Asexual propagation techniques in Germany have shown that the characteristics of the new variety are homogeneous, stable, and strictly transmissible by such asexual propagation from one generation to another. Accordingly, the new variety undergoes asexual propagation in a true-to-type manner.

The new variety has been named 'KORroleotu'.

BRIEF DESCRIPTION OF THE PHOTOGRAPHS

The accompanying photographs show, as nearly true as it is reasonably possible to make the same in color illustrations of this character, typical specimens of the new variety. The illustrated rose plants of the new variety were approximately three years of age and were observed during July 2017 while growing outdoors on understock in The Hauge, Netherlands.

Figure 1:
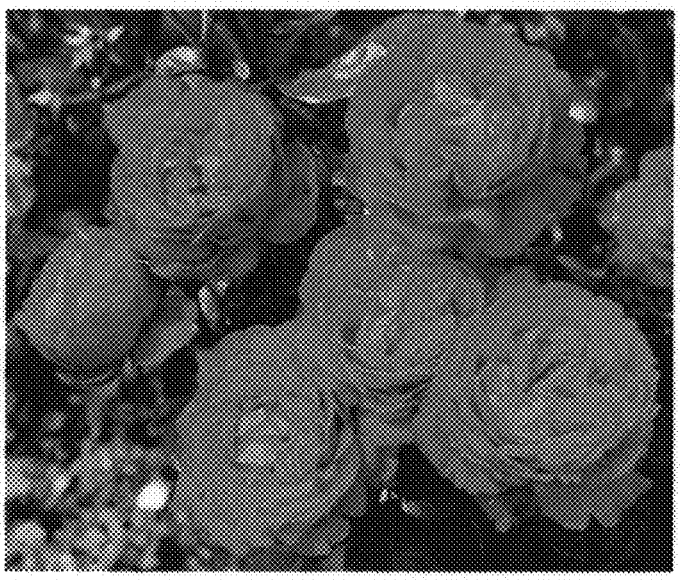

FIG. 1—illustrates a specimen of a plant displaying blossoms in the course of opening.

Figure 2:
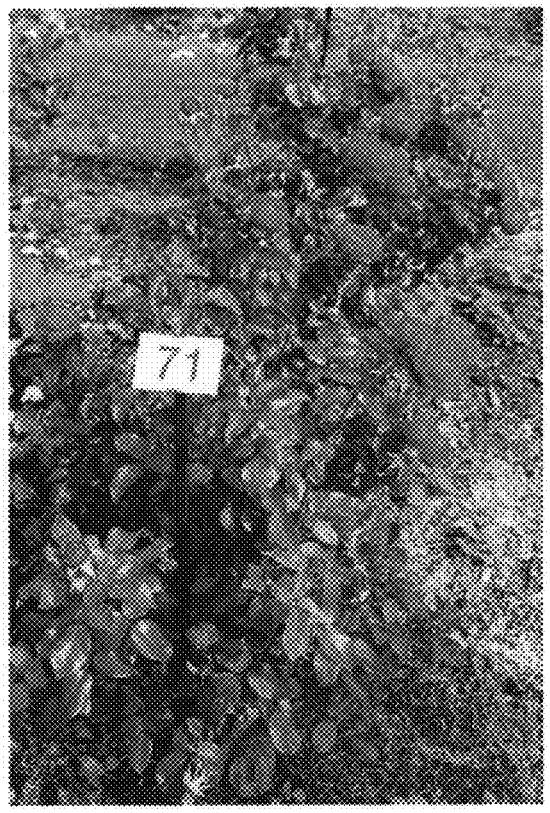

FIG. 2—illustrates specimens of plants displaying floral buds and flowers at varying points of opening.

DETAILED BOTANICAL DESCRIPTION

The chart used in the identification of colors is that of The Royal Horticultural Society (R.H.S. Colour Chart), 2015, London, England. The terminology which precedes reference to the chart has been added to indicate the corresponding color in more common terms. The description is based on the observation of one-year-old specimen of the new variety during July while growing in a one-gallon container on its own roots in Cochranville, Pa.

Class: Grandiflora Rose Plant.

Plant:

*Habit*.—Very bushy and upright growth.

*Height*.—Commonly near 48.0 cm, measured from the top of the soil plane.

*Width*.—Commonly near 48.0 cm.

Branches:

*Color*.—Young stems: commonly near Yellow-Green Group 146A. Old wood: commonly near Yellow-Green Group 146A transistions to Greyed-Orange Group 177A.

*Length*.—Main stem: approximately 17.0 cm on average. Secondary stems: approximately 9.0 cm on average.

*Thorns*.—Young thorns: color is commonly near Greyed-Orange Group 176C; length is approximately 3.0 mm on average; width is approximately 1.0 mm on average at point of attachment. Old thorns: color is commonly near Greyed-Orange Group 176C; length is approximately 5.0 mm on average; width is approximately 2.0 mm on average at point of attachment.

Foliage:

*General appearance*.—Glossy, dark green.

*Young foliage color*.—Upper surface: commonly near Yellow-Green Group 144A and commonly near Greyed-Purple Group 184A at the leaf margins. Under surface: commonly near Greyed-Orange Group 176B and near Yellow-Green Group 146B.

*Old foliage color*.—Upper surface: commonly near Green Group 139A. Under surface: commonly near Green Group 138A.

5-*leaflet leaf*.—Length: Approximately 12.5 cm on average. Width: approximately 8.0 cm on average.

Leaflets:

*Number*.—Commonly 3, 5, and 7.

*Shape*.—Ovate.

*Margin*.—Serrate.

*Texture*.—Upper surface and under surface: smooth.

*Terminal leaflet*.—Length: approximately 5.0 cm on average. Width: approximately 3.8 cm on average.

*Lower leaflet*.—Length: approximately 3.0 cm on average. Width: approximately 2.9 cm on average.

*Rachis*.—Color of upper surface: commonly near Green Group NN137A. Color of under surface: commonly near Green Group 137A.

*Petiole*.—Texture of upper surface: smooth. Texture of under surface: glandular with some small prickles. Color of upper surface: commonly near Green Group NN137A. Color of under surface: commonly near Green Group 137C.

*Stipules*.—Length: approximately 9.0 mm on average. Width: approximately 6.0 mm on average. Margin: entire to erose. Color of upper surface: commonly near Green Group 137B. Color of lower surface: commonly near Green Group 137C.

Inflorescence:

*Number of flowers*.—Generally about 3 blooms on a plant at once, on average.

*Number of blossoms per stem*.—Commonly between 1 bloom per stem on average.

*Bud*.—Shape: ovoid. Length: approximately 1.5 cm on average. Width: approximately 1.5 cm on average. Color when opening: commonly near Red Group 53A.

*Sepals*.—Number: commonly 5. Length: approximately 1.6 cm on average. Width: approximately 1.0 cm on average. Margin: entire with occasional extensions on two or three sepals measuring 2.0 mm in length and 1.0 mm in width. Upper surface: texture: covered in short pubescence. color: commonly near Yellow-Green Group 144A. Under surface: texture: puberulent. color: commonly near Yellow-Green Group 144B.

*Peduncle*.—Length: approximately 6.0 cm on average. Diameter: approximately 3.0 mm on average. Surface texture: sparely covered in short, flexible thorns that measure less than 2.0 mm in length. Color: commonly near Yellow-Green Group 146B.

*Flower*.—Form: double, cuplike. Diameter: approximately 6.5 cm on average. Height: approximately 4.5 cm on average. Duration: on the plant approximately 10 days, on average. Color: upper surface and under surface commonly near Red Group N45A. Fragrance: very light sweet fragrance. Number of petals: approximately 95 on average. Petal drop: good. Shape of the petal: overall: broadly obovate. apex: round. base: cuneate. Petal length: approximately 2.5 cm on average. Petal width: approximately 2.0 cm on average. Petal margin: entire. Petaloids number: commonly 10 per flower on average. Petaloids length: approximately 1.5 cm on average. Petaloids width: approximately 9.0 mm on average. Petaloids texture: smooth. Petaloid shape: variable, oblong and mostly curving inward. apex: round. base: cuneate. Petaloids margins: variable, entire to erose. Petaloid color: upper surface and under surface are commonly near Yellow Group 10C. Stamen: number is approximately 67 on average. Anthers: number is approximately 35 on average and color is commonly near Yellow-Orange Group 22B. Filaments: length is approximately 3.0 mm on average and color is commonly near Yellow-Green Group 151C. Pistils: arrangement is separate and free and number is approximately 121 on average. Style: length is approximately 1.0 cm on average and color is commonly near Yellow-Green Group 150D and Red-Purple Group 63B. Stigma: diameter is less than 1.0 mm on average and color is commonly near Yellow-Green Group 150D. Receptacle: achenes stand on the bottom and wall; diameter is approximately 1.0 cm on average; shape is round; surface texture is smooth; and color is commonly near Yellow-Green Group 144A. Pollen: commonly low amount, color is commonly near Greyed-Orange Group 163A.

Development:

*Vegetation*.—Vigorous and glossy, dark green.

*Blooming*.—Abundant and substantially continuous from spring through frost.

*Tolerance to diseases*.—Very good.

Plants of the 'KORroleotu' variety have not been observed under all possible environmental conditions to date. Accordingly, it is possible that the phenotypic expression may vary somewhat with changes in light intensity and duration, cultural practices, and other environmental conditions.

I claim:

1. A new and distinct Grandiflora Rose Plant characterized by the following combination of characteristics:

(a) abundantly and substantially continuously forms attractive, red colored blossoms, (b) exhibits a very bushy and upright growth habit, (c) forms vigorous vegetation, (d) forms attractive ornamental glossy, dark green foliage, and (e) exhibits very good disease resistance;

substantially as herein shown and described.

* * * * *